United States Patent
Yajima et al.

(10) Patent No.: US 8,912,508 B2
(45) Date of Patent: Dec. 16, 2014

(54) MULTIPHOTON-EXCITED MEASURING DEVICE

(75) Inventors: Hiroyoshi Yajima, Kanagawa (JP); Kenji Taira, Tokyo (JP)

(73) Assignee: Olympus Corporation, Tokyo (JP)

( * ) Notice: Subject to any disclaimer, the term of this patent is extended or adjusted under 35 U.S.C. 154(b) by 283 days.

(21) Appl. No.: 12/677,952

(22) PCT Filed: Mar. 24, 2009

(86) PCT No.: PCT/JP2009/055823
§ 371 (c)(1),
(2), (4) Date: Mar. 12, 2010

(87) PCT Pub. No.: WO2009/157235

PCT Pub. Date: Dec. 30, 2009

(65) Prior Publication Data

US 2010/0224794 A1     Sep. 9, 2010

(30) Foreign Application Priority Data

Jun. 24, 2008 (JP) ................. 2008-164132

(51) Int. Cl.
*G01N 21/64* (2006.01)
*G02B 21/08* (2006.01)

(52) U.S. Cl.
CPC .......... *G01N 21/6458* (2013.01); *G02B 21/082* (2013.01); *G01N 2201/0697* (2013.01)
USPC .................................................... 250/458.1

(58) Field of Classification Search
CPC ....................... G01N 2201/0697; G02B 21/082
USPC ...................................................... 250/458.1
See application file for complete search history.

(56) References Cited

U.S. PATENT DOCUMENTS 5,168,164 A * 12/1992 Urakami et al. ........... 250/458.1
2002/0027202 A1* 3/2002 Engelhardt et al. ........ 250/458.1

(Continued)

FOREIGN PATENT DOCUMENTS

JP       11-218490      8/1999
JP       2005-172776    6/2005

(Continued)

OTHER PUBLICATIONS

James van Howe, Jennifer H. Lee, Shian Zhou, Frank Wise, Chris Xu, Siddharth Ramachandran, Samir Ghalmi, and Man F. Yan, "Demonstration of soliton self-frequency shift below 1300nm in higher-order mode, solid silica-based fiber." Optics Letters, vol. 32, No. 4 (Feb. 15, 2007) pp. 340-342. Downloaded May 22, 2013. <doi:10.1364/OL.32.000340>.*

(Continued)

*Primary Examiner* — Constantine Hannaher
(74) *Attorney, Agent, or Firm* — Scully, Scott, Murphy & Presser, P.C.

(57) ABSTRACT

A multiphoton-excited measuring device measuring a sample with the use of a multiphoton absorption phenomenon by optical pulses having high intensity, comprising a short pulse light source 2 emitting optical pulses; an irradiation optical system 17, 18, 19 irradiating a sample 20 with optical pulses emitted from the short pulse light source 2; a detector 24 detecting signal light generated, in association with multiphoton excitation, from the sample 20 by the irradiation with optical pulses; and an optical pulse compression means 4, 13 compressing a pulse width, with the use of intensity-dependent nonlinear effects of the optical fiber 4, so that a pulse width of optical pulses with which the sample 20 is to be irradiated is shorten to equal to or narrower than that of optical pulses emitted from the short pulse light source 2 and so that a spectral width of optical pulses with which the sample 20 is to be irradiated is wider than that of optical pulses emitted from the short pulse light source 2, which makes it possible to stably irradiate, with the use of easy-to-use short pulse light source, a sample with optical pulses having higher peak intensity and a shorter temporal width and measure the sample easily with high accuracy without requiring sophisticated laser techniques and skills.

10 Claims, 6 Drawing Sheets

(56) References Cited

U.S. PATENT DOCUMENTS

| | | | |
|---|---|---|---|
| 2003/0007205 A1* | 1/2003 | Lee et al. | 359/110 |
| 2004/0071423 A1* | 4/2004 | Libori et al. | 385/127 |
| 2005/0279950 A1 | 12/2005 | Kawano et al. | |
| 2006/0002715 A1* | 1/2006 | Igarashi et al. | 398/152 |
| 2006/0237666 A1 | 10/2006 | Kubo | |
| 2009/0021746 A1 | 1/2009 | Toida et al. | |

FOREIGN PATENT DOCUMENTS

| | | |
|---|---|---|
| JP | 2005-257507 | 9/2005 |
| JP | 2005-257509 | 9/2005 |
| JP | 2006-195240 | 7/2006 |
| JP | 2006-330685 | 12/2006 |
| JP | 2008-122278 | 5/2008 |

OTHER PUBLICATIONS

International Search Report dated Jun. 23, 2009, in PCT/JP2009/055823.

Japanese Office Action dated Oct. 30, 2012 from corresponding Japanese Patent Application No. 2008-164132, together with an English language translation.

\* cited by examiner

MULTIPHOTON-EXCITED MEASURING DEVICE

CROSS REFERENCE TO RELATED APPLICATION

This application claims priority to and the benefit of Japan Patent Application No. 2008-164132 filed on Jun. 24, 2008, the entire content of which is incorporated herein by reference.

TECHNICAL FIELD

This invention relates to a multiphoton-excited measuring device irradiating a sample with short pulse light having a high peak light intensity so as to measure the sample with the use of the multiphoton absorption phenomenon.

BACKGROUND ART

As a conventional multiphoton-excited measuring device, there is known a multiphoton-excited microscope system such as one shown in FIG. 6, for example (see Patent Document 1, for example). In the multiphoton-excited microscope system, a short pulse laser light source 101 having a titanium-sapphire laser emits an optical pulse I with a pulse width of about 100 fs and a spatial distribution being of nearly perfect circle, and the optical pulse I transmits through free space to be incident on a pre-chirping unit 102.

The pre-chirping unit 102 has four diffraction gratings 121, 122, 123 and 124, and the incident optical pulse I is first diffracted and reflected, with respect to each of wavelength components thereof, in a different angular direction in the plane of the paper in FIG. 6 by the diffraction grating 121. It is noted that the angular direction to which wavelength components of the optical pulse I are reflected by the diffraction grating 121 in the vertical direction of the plane of the paper in FIG. 6, is constant. Next, the optical pulse I is diffracted and reflected by the diffraction grating 122 with respect to each of wavelength components in the same way. The spatial distribution of the optical pulse I after diffracted by the diffraction grating 122 is elliptical with a vertical direction of the plane of the paper in FIG. 6 as a long axis when seen from a transmitted direction of the optical pulse I. Thereafter, the optical pulse I is sequentially diffracted and reflected by the diffraction gratings 123, 124 in the same way as by the diffraction gratings 121, 122, and emitted from the pre-chirping unit 102 after its spatial distribution becomes of nearly perfect circle again.

As above, the optical pulse I is sequentially diffracted by four diffraction gratings 121, 122, 123, 124 in the pre-chirping unit 102, thereby the temporal width of the optical pulse I is expanded, before or after the pre-chirping unit 102, to temporally ahead for its short wavelength components and behind for its long wavelength components due to the difference of transmission distance depending on wavelength components. Such a state of optical pulse is generally referred to as a chirp pulse. In FIG. 6, the schematic time waveform of the optical pulse I is also represented with a horizontal axis as time and a vertical axis as a light intensity.

The optical pulse I emitted from the pre-chirping unit 102 transmits through free space and passes through a coupling device 103 to be incident on a single-mode optical fiber 104. The single-mode optical fiber 104 has a difference in a transmission speed for a wavelength which is called wavelength dispersion, and a zero-dispersion wavelength determined based on materials or the like distinguishes between a normal dispersion region and an anomalous dispersion region. In the normal dispersion region, the transmission speed of light is higher with a long wavelength than with a short wavelength, and the opposite is in the anomalous dispersion region. Here, the single-mode optical fiber 104 normally-diffuses the optical pulse I. Therefore, the optical pulse I in which short wavelength components are temporally ahead transmits through the single-mode optical fiber 104, and then long wavelength components which have been temporally behind catch up with short wavelength components which have been temporally ahead, resulting in the formation of a time waveform similar to one at the time the optical pulse I is oscillated from the short pulse laser light source 101.

The optical pulse I having transmitted through the single-mode optical fiber 104 is incident on a microscope 105. With respect to the optical pulse I incident on the microscope 105, a coupling optical system 151 expands its spatial distribution to render the pulse to be parallel light. It is noted that a pinhole 152 is disposed at a light focus point of the optical pulse I in the coupling optical system 151 to remove light noises of the optical pulse I. Subsequently, the optical pulse I is reflected by a dichroic mirror 153 and collected on a sample 156 by an image-forming optical system 155. It is noted that a scan unit 154 scans the light focus point of the optical pulse I on the sample 156 in a plane perpendicular to a light axis of the image-forming optical system 155.

When the sample 156 is irradiated with the optical pulse I, dye or fluorescent substances in the sample 156 are multiphoton excited, generating fluorescence. The fluorescence generated in the sample 156 transmits in the opposite direction of the incident direction of the optical pulse I, passes through the image-forming optical system 155 and the scan unit 154 and is incident on the dichroic mirror 153 to pass therethrough. Subsequently, the fluorescence having transmitted through the dichroic mirror 156 is focused onto the pinhole 158 by an image-forming optical system 157 for detection, and then incident on a detector 159 to be detected as signals. It is noted that the pinhole 158 has functions improving the resolution of the sample 156 in a light axis direction. Such a multiphoton-excited microscope system is generally referred to as a confocal laser scanning multiphoton-excited fluorescence microscope system.

Patent Document: JP 11-218490 A

DISCLOSURE OF THE INVENTION

Problems to be Solved by the Invention

In the multiphoton-excited microscope system such as one shown in FIG. 6, the excitation efficiency with which dye or fluorescent substances in the sample are multiphoton-excited is proportional to the square of the peak intensity of irradiated optical pulses. That is, when the same optical pulse energy is provided, the peak intensity of the optical pulse is higher with a shorter temporal width, so that stronger fluorescence can be generated.

When the multiphoton excitation is performed, therefore, it is important how optical pulses having a high peak intensity are obtained on a sample. In addition, when a sample is biological one, it is required to limit irradiation to with small energy so as to avoid damages due to optical irradiation. Thus, it is necessary to irradiate the sample with optical pulses having a shorter temporal width.

However, when the optical pulse transmits substances like optical fibers, the pulse width is expanded by dispersion effects in which a transmission speed varies for each wavelength held by a substance and, due to the difference in the sign of dispersion, the wavelength of the optical pulse varies between the prior side of the time axis and the later side thereof. Moreover, substances like the optical fiber have nonlinear effects, and thus when an optical pulse having a very high peak intensity is incident, the optical pulse is deteriorated by a phenomenon referred to as self phase modulation in which a wavelength distribution of the optical pulse is varied by the nonlinear effects of the substances.

For this reason, in the conventional multiphoton-excited microscope system shown in FIG. 6, the pre-chirping unit 102 is inserted between the short pulse laser light source 101 and the single-mode fiber 104 as the optical fiber to expand the temporal width of the optical pulse, thereby the peak intensity is lowered and the generation of self phase modulation is suppressed. Moreover, anticipating the addition of dispersion by the single-mode fiber 104, the expanded optical pulse is recompressed so that the optical pulse having high peak intensity is incident on the microscope 105. Thus, the relation between the temporal width of the optical pulse I emitted by the short pulse laser light source 101 (t1) and the temporal width of the optical pulse I on the sample 156 in the microscope 105 (t2) is represented as t1≤t2. Here, t1=t2 is a condition in an ideal state, and most cases are of t1<t2.

Therefore, in the conventional configuration, it is required to emit optical pulses having a shorter temporal width from a short pulse laser light source itself in order to obtain optical pulses having a higher peak intensity and a shorter temporal width with which the efficiency of multiphoton excitation is improved when the same pulse energy is provided.

However, with respect to such a short pulse laser light source, its laser operation is very unstable and the handling thereof requires sophisticated laser techniques and skills. Thus, it could be possible that the measurement of the sample with high accuracy becomes difficult.

Therefore, an object of the invention made in view of the above aspects is to provide a multiphoton-excited measurement device capable of stably irradiating, with the use of easy-to-use short pulse light source, a sample with optical pulses having a higher peak intensity and a shorter temporal width and measuring the sample easily with high accuracy without requiring sophisticated laser techniques and skills.

SUMMARY OF THE INVENTION

A first aspect of the invention for achieving the above object is a multiphoton-excited measuring device measuring a sample with the use of a multiphoton absorption phenomenon by optical pulses having high intensity, comprising
 a short pulse light source emitting optical pulses;
 an irradiation optical system irradiating a sample with optical pulses emitted from the short pulse light source;
 a detector detecting signal light generated, in association with multiphoton excitation, from the sample by the irradiation with optical pulses; and
 an optical pulse compression means being disposed between the short pulse light source and the irradiation optical system and including an optical fiber transmitting optical pulses emitted from the short pulse light source to compress a pulse width, with the use of nonlinear effects causing intensity-dependent spectral variation of the optical fiber, so that a pulse width of optical pulses with which the sample is to be irradiated is shorten to equal to or narrower than that of optical pulses emitted from the short pulse light source and so that a spectral width of optical pulses with which the sample is to be irradiated is broader than that of optical pulses emitted from the short pulse light source.

A second aspect of the invention is a multiphoton-excited measuring device according to the first aspect,
 wherein the optical fiber included in the optical pulse compression means is constituted by a single-mode optical fiber expanding a spectral width and providing positive group-velocity dispersion for optical pulses emitted from the short pulse light source; and
 the optical pulse compression means comprises a negative dispersion compensation means providing negative group-velocity dispersion for optical pulses having transmitted through the single-mode optical fiber.

A third aspect of the invention is a multiphoton-excited measuring device according to the second aspect, wherein the negative dispersion compensation means comprises any one of a pair of diffraction gratings, a pair of prisms or a pair of grisms.

A fourth aspect of the invention is a multiphoton-excited measuring device according to the first aspect,
 wherein the optical fiber included in the optical pulse compression means is constituted by a single-mode optical fiber expanding a spectral width and providing positive group-velocity dispersion for optical pulses emitted from the short pulse light source; and
 the optical pulse compression means comprises a single-mode hollow core optical fiber with a hole in a cross-section thereof providing negative group-velocity dispersion for optical pulses having transmitted through the single-mode optical fiber.

A fifth aspect of the invention is a multiphoton-excited measuring device according to the first aspect, wherein the optical fiber included in the optical pulse compression means is constituted by a single-mode optical fiber expanding a spectral width and providing negative group-velocity dispersion for optical pulses emitted from the short pulse light source.

A sixth aspect of the invention is a multiphoton-excited measuring device according to any one of the first to fifth aspects, wherein a pulse width of optical pulses emitted from the short pulse light source is of picosecond and a pulse width of optical pulses with which the sample is irradiated is of femtosecond.

A seventh aspect of the invention is a multiphoton-excited measuring device according to any one of the first to sixth aspects, wherein a repetition rate of optical pulses emitted from the short pulse light source is variable.

An eighth aspect of the invention is a multiphoton-excited measuring device according to any one of the first to seventh aspects, wherein the short pulse light source comprises a gain switched laser diode.

A ninth aspect of the invention is a multiphoton-excited measuring device according to any one of the first to seventh aspects, wherein the short pulse light source comprises an active-mode locked fiber-ring laser.

A tenth aspect of the invention is a multiphoton-excited measuring device according to the first aspect, wherein the optical pulse compression means is removable.

An eleventh aspect of the invention is a multiphoton-excited measuring device according to any one of the first to tenth aspects, wherein the multiphoton-excited measuring device is a multiphoton-excited fluorescence microscope system detecting, by the detector, fluorescence generated from the sample in association with multiphoton excitation.

Effect of the Invention

In the invention, an optical pulse compression means including an optical fiber is disposed between a short pulse light source and an irradiation optical system, and pulse width compression is conducted, using the nonlinear effects causing intensity-dependent spectral variation of the optical fiber, so that the pulse width of the optical pulse with which a sample is to be irradiated is shorten to equal to or narrower than that of the optical pulse emitted from the short pulse light source and so that the spectral width of the optical pulse with which the sample is to be irradiated is wider than that of the optical pulse emitted from the short pulse light source. Thereby, it is possible to stably irradiate, with the use of the easy-to-use short pulse light source, a sample with optical pulses having a higher peak intensity and a shorter temporal width and then measure the sample easily with high accuracy without requiring sophisticated laser techniques and skills.

REFERENCE SYMBOLS 1 multiphoton-excited laser scanning fluorescence microscope system
  2 short pulse light source
  3 laser scanning microscope
  4 single-mode optical fiber
  5 electrical pulse generator
  6 laser diode
  7 single-mode optical fiber
  8 fiber amplifier
  9 fiber amplifier
  10 optical fiber connector
  11 optical fiber connector
  12 mirror
  13 negative dispersion compensation means
  14 reflective mirror
  15 mirror
  16 two-dimensional scan means
  17 pupil-projection lens
  18 image-forming lens
  19 objective lens
  20 sample
  21 dichroic mirror
  23 collective lens
  24 detector
  26 collimate lens
  31 diffraction grating
  32 diffraction grating
  33 reflective mirror
  41 single-mode hollow core optical fiber
  42 single-mode optical fiber
  50 active-mode locked fiber-ring laser
  51 demultiplexing coupler
  52 gain unit
  53 band-pass filter
  54 single-mode optical fiber
  55 signal generator
  56 isolator
  57 dispersion compensation means

BEST MODE FOR CARRYING OUT THE INVENTION

Embodiments of the invention will be described below using an example of a multiphoton-excited laser scanning fluorescence microscope system with reference to the accompanying drawings.

First Embodiment

Figure 1:
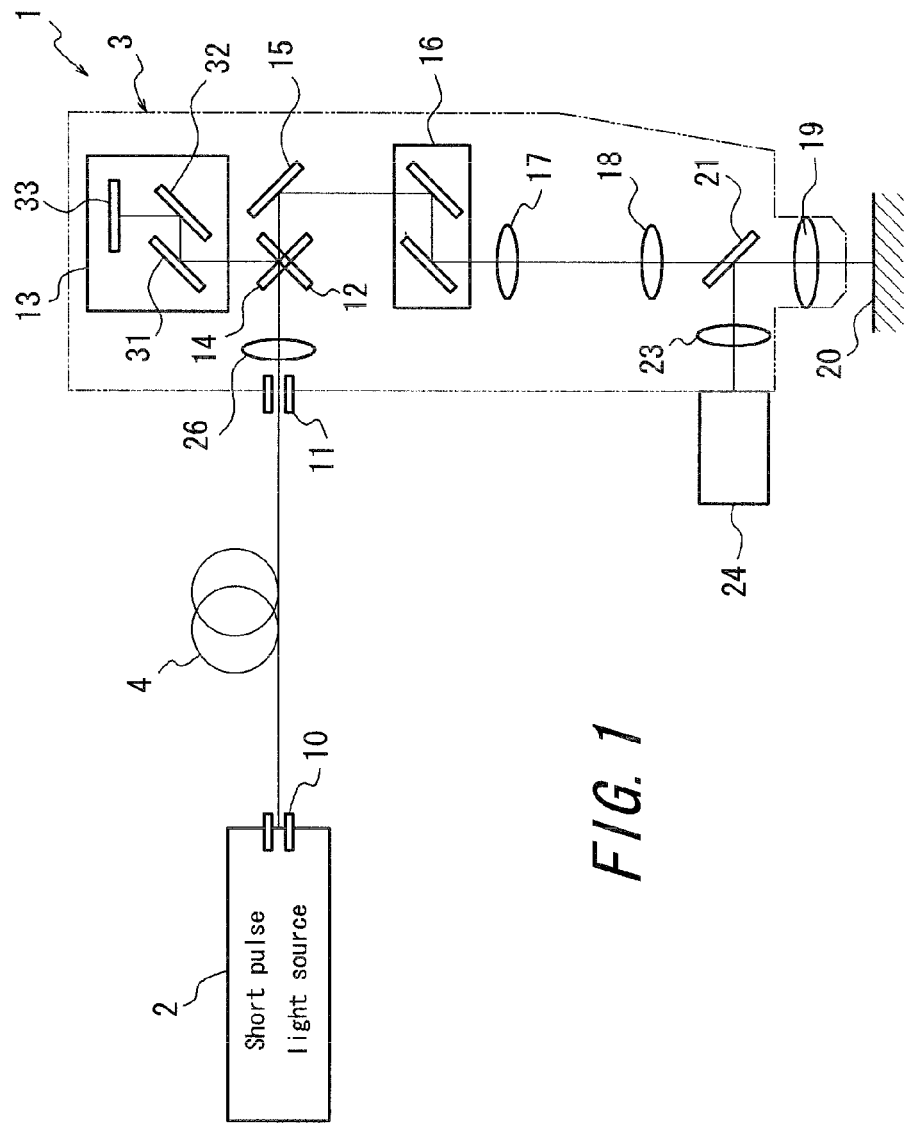
FIG. 1 is a diagram illustrating a configuration of a main part of the multiphoton-excited laser scanning fluorescence microscope system according to the first embodiment of the invention.

FIG. 1 is a diagram illustrating a configuration of a main part of the multiphoton-excited laser scanning fluorescence microscope system according to the first embodiment of the invention. The multiphoton-excited laser scanning fluorescence microscope system 1 has a short pulse light source 2, a laser scanning microscope 3 and a single-mode optical fiber 4 so that optical pulses emitted from the short pulse light source 2 are rendered to be incident on the laser scanning microscope 3 through the single-mode optical fiber 4 and collected on a sample 20. With respect to the single-mode optical fiber 4, one end portion (incidence end portion) thereof is optically and mechanically connected removably to an optical fiber connector 10 provided in the short pulse light source 2, and the other end portion (output end portion) is optically and mechanically connected removably to an optical fiber connector 11 provided in the laser scanning microscope 3. Thus, the short pulse light source 2 and the laser scanning microscope 3 are optically connected through the single-mode optical fiber 4 in an arbitrary layout.

The sample 20 is a living cell in which fluorescent protein is expressed, and the optical pulses collected on the sample 20 generate fluorescence through excitation by multiphoton absorption of fluorescent protein. In the case of two-photon excitation, the intensity of the fluorescence is proportional to the square of average optical power of the excitation optical pulse and is inversely proportional to the temporal width and the repetition rate of the optical pulse.

Figure 2:
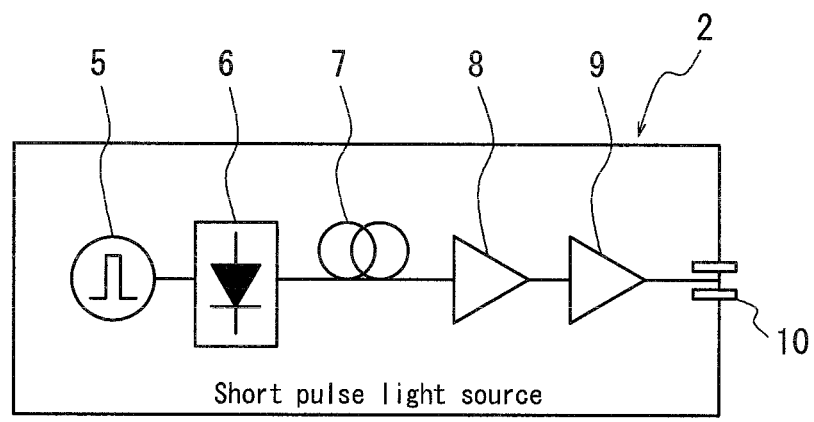
FIG. 2 is a diagram illustrating an example of a configuration of a main part of the short pulse light source shown in FIG. 1.

FIG. 2 is a diagram illustrating an example of a configuration of a main part of the short pulse light source 2 shown in FIG. 1. The short pulse light source 2 has an electrical pulse generator 5, a laser diode 6, a single-mode optical fiber 7, fiber amplifiers 8, 9 and an optical fiber connector 10.

The electrical pulse generator 5 generates electrical pulses having a width of several hundreds to several thousands of picoseconds, and supplies an electric current to the laser diode 6 through the electrical pulses. In the embodiment, a repetition rate of the electrical pulses generated from the electrical pulse generator 5 is variable. Here, the repetition rate of the electrical pulse is variable within a range from 1 MHz to 200 MHz (pulse interval of 5 ns to 1 µs). Thus, it is possible to change the repetition rate of the optical pulse emitted from the short pulse light source 2 easily and stably.

The laser diode 6 is activated by so-called gain-switching for which a gain is instantaneously generated and disappeared by the electric current injected through electrical pulses from the electrical pulse generator 5, thus generating optical pulses having a width of a few tens of picoseconds temporally-chirped from a short wavelength to a long wavelength. As the laser diode 6, there can be used a vertical cavity surface emitting laser (VCSEL), a quantum-well distributed feedback laser diode (QWDFBLD) or a quantum dot distributed feedback laser diode (QDDFBLD), for example, and the VCSEL is used in the embodiment. Moreover, the wavelength of the optical pulse may be a wavelength suitable for multiphoton excitation for the sample 20, and visible, near-infrared and infrared light can be used. Here, there is used near-infrared light with a band of 980 nm.

The optical pulse generated from the laser diode 6 is rendered to be incident on the single-mode optical fiber 7. The single-mode optical fiber 7 compensates the chirp in a way that the long wavelength side of the incident optical pulse is transmitted earlier than the short wavelength side thereof thorough positive group-velocity dispersion (GVD), and thus converts the incident optical pulse to a transform-limited (TL) optical pulse having a width of a few picosecond. Thus, the length of the single-mode optical fiber 7 is set based on group-velocity dispersion amount per unit length and chirp amount of optical pulses to be corrected. In the embodiment, the length of the single-mode optical fiber 7 is set to be about 1 km.

It is noted that the product of the temporal width of the TL optical pulse and the bandwidth of the wavelength (optical spectral width) may be a minimum value, and a wider optical spectral width is required to obtain an optical pulse having a shorter temporal width. In the embodiment, the VCSEL is used as the laser diode 6, and the optical spectral width of oscillated wavelength therefrom is about 1 nm. Thus, the temporal width of the TL optical pulse is about 3 ps to 5 ps.

The optical pulse having transmitted through the single-mode optical fiber 7 is sequentially amplified by two fiber amplifiers 8, 9. The fiber amplifiers 8, 9 use a single clad or a double clad optical fiber which is excited by a fiber laser or a laser diode and doped with Nd, Yb, Tm or Er as a medium to be excited, or an optical fiber having a hollow in its cross-section. Here, there is used a single clad optical fiber doped with Yb as a medium to be excited, and the Yb-doped optical fiber is excited using a laser diode having a wavelength of 940 nm to generate an amplification gain for a band of 980 nm. These two fiber amplifiers 8, 9 amplify the optical pulse having transmitted through the single-mode optical fiber 7 to an optical pulse having an average light intensity (average output) of several tens of mW to several W, thereafter the optical pulse passes through the optical fiber connector 10 and is output from the short pulse light source 2.

As the optical fiber connector 10, there can be used various connectors of SC, FC, ST, MU and LC type. The embodiment uses the FC type.

In the embodiment, the optical pulse generated from the short pulse light source 2 has nearly constant average output power (optical pulse energy×repetition rate) as the average light intensity, and the pulse width (temporal width of the optical pulse) is also nearly constant according to a repetition rate. Therefore, provided that the pulse width is constant and the average output power is also constant, the energy per optical pulse increases and the peak light intensity becomes higher when the repetition rate lowers. That is, the peak light intensity of the optical pulse is inversely proportional to the repetition rate.

It is noted that all components are connected via the optical fiber in the short pulse light source 2 and a polarization maintaining optical fiber is adequately used to suppress the instability of operation due to the instability of the polarization state. Moreover, an optical isolator is adequately inserted so as to prevent damages to the laser diode 5 and the fiber amplifiers 8, 9 due to reflected light, and an optical filter is adequately inserted so as to obtain an optimum optical spectrum waveform.

In FIG. 1, the optical pulse oscillated from the short pulse light source 2 is rendered to be incident on the single-mode optical fiber 4 through the optical fiberconnector 10. The single-mode optical fiber 4 has a length of a few tens of meters and has normal dispersion in a band with a wavelength of 980 nm.

With respect to the optical pulse having been incident on the single-mode optical fiber 4, the chirp is generated in the single-mode optical fiber 4 by self phase modulation (SPM) as nonlinear (optical) effects due to its high peak light intensity, and the light spectrum is expanded with keeping the same optical pulse width. At the same time, the optical pulse is temporally chirped from a long wavelength to a short wavelength by positive group-velocity dispersion (GVD), and the optical pulse width is expanded to a few picoseconds to a few tens of picoseconds. Thereafter, the optical pulse is emitted from the single-mode optical fiber 4. Here, nonlinear (optical) effects causing intensity-dependent spectral variation of the optical pulse are the optical Kerr effect, the stimulated Raman scattering effect and the like.

The optical pulse emitted from the single-mode optical fiber 4 is introduced into the laser scanning microscope 3 through the FC-type optical fiber connector 11, for example, same as the optical fiber connector 10 provided in the short pulse light source 2.

The laser scanning microscope 3 has a collimate lens 26, a mirror 12, a negative dispersion compensation means 13, a reflective mirror 14, a mirror 15, a two-dimensional scan means 16, a pupil-projection lens 17, an image-forming lens 18, an objective lens 19, a dichroic mirror 21, a collective lens 23 and a detector 24, in addition to the optical fiber connector 11.

The optical pulse introduced into the laser scanning microscope 3 is output to a free space system and rendered to be nearly parallel light by the collimate lens 26, then being incident on the negative dispersion compensation means 13 by reflection by the mirror 12. The negative dispersion compensation means 13 can be of small size with being constituted by two diffraction gratings 31, 32 and a reflective mirror 33. The optical pulse having been incident on the negative dispersion compensation means 13 is diffracted by the diffraction grating 31 first, and emitted at an angle different for each wavelength component. Subsequently, the optical pulse is diffracted by the diffraction grating 32 to become parallel light. In this state, the spatial distribution of the optical pulse is of elliptical shape, which has been changed from circular shape at the time of incidence. Thereafter, the optical pulse is reflected by the reflective mirror 33 in parallel with the incident light at a different height position from incident height position in a direction parallel with a groove of the reflective diffraction gratings 31, 32, and is sequentially diffracted again by two diffraction gratings 32, 31. Thus, the optical pulse has an original circular shape of spatial distribution, and is emitted from the negative dispersion compensation means 13, thereafter it is reflected by the reflective mirror 14 to return onto the original light path.

The negative dispersion compensation means 13 provides negative group-velocity dispersion to the optical pulse. Since the negative group-velocity dispersion compensates the chirp of the optical pulse and the optical spectral width has been expanded, the optical pulse having a width of a few picoseconds output from the short pulse light source 2 is stably and efficiently compressed to the optical pulse having a width of a few hundreds of femtoseconds. Here, the optical pulse having a pulse width of 3 ps to 5 ps oscillated from the short pulse light source 2 is compressed to have a width of 200 fs to 300 fs. It is noted that the negative group-velocity dispersion means is constituted not only by reflective diffraction gratings 31, 32, but also by a transmissive grating, a prism, a grism and the like so that the pulse can be stably and efficiently compressed with its small constitution in the same way. Moreover, although the negative dispersion compensation means 13 is disposed inside the laser scanning microscope 3 in FIG. 1, it can be constituted as a separate component from the laser scanning microscope 3 and disposed separately from or adjacently to the laser scanning microscope 3.

The optical pulse having passed through the negative dispersion compensation means 13 is reflected by the mirror 15 and incident on a two-dimensional scan means 16, in which the transmission angle from a light axis is scanned. The two-dimensional scan means 16 is constituted by so-called proximal galvano scanner mirrors in which there are adjacently disposed two galvano scanner mirrors which can be oscillated around two axes perpendicular to each other, for example.

The optical pulse having passed through the two-dimensional scan means 16 are collected by a pupil-projection lens 17 so as to form an intermediate image, and then rendered to be parallel light by an image-forming lens 18. Thereafter, they pass through the dichroic mirror 21 to be collected on a sample 20 by an objective lens 19. Thus, an object to be measured (fluorescent protein, for example) in the sample 20 is multiphoton excited, so that fluorescence by multiphoton excitation is generated from the sample 20. In the embodiment, therefore, the irradiation optical system is constituted including the pupil-projection lens 17, the image-forming lens 18 and the objective lens 19. Moreover, the single-mode optical fiber 4 and the negative dispersion compensation means 13 constitute the optical pulse compression means.

The fluorescence generated from the sample 20 passes through the objective lens 19 to be incident on the dichroic mirror 21. Since the fluorescence has a wavelength different from that of the optical pulse collected on the sample 20, it is reflected by the dichroic mirror 21 and collected by a collective lens 23 into a detector 24 to be converted to electrical signals.

In the embodiment, the average output of the optical pulse generated from the short pulse light source 2 is nearly constant relative to the repetition rate of the optical pulse. Therefore, the SPM and the positive GVD by nonlinear effects of the single-mode optical fiber 4 and pulse width compression by nonlinear pulse compression action of the negative dispersion compensation means 13 cause the optical pulse to have a higher peak intensity and, in addition, the repetition rate of the optical pulse is lowered, which enables further higher peak intensity. Thus, since the fluorescent intensity by multiphoton excitation is proportional to the square of average optical power of the excitation optical pulse and is inversely proportional to the temporal width and the repetition rate of the optical pulse, as described above, the fluorescent intensity can be increased by changing a repetition rate of the optical pulse without changing average irradiation energy (average light intensity) significantly affecting damages, when the sample 20 is a living cell, to the living cell.

As above, in the embodiment, with using the expansion of the optical spectral width through nonlinear effects by the single-mode optical fiber 4 optically connecting the short pulse light source 2 with the laser scanning microscope 3 and the chirp by positive group-velocity dispersion, the temporal width of the optical pulse having passed through the single-mode optical fiber 4 is compressed by the negative dispersion compensation means 13 having two diffraction gratings 31, 32 so as to increase the peak light intensity of the optical pulse. Therefore, the short pulse light source 2 can be configured to generate optical pulses having a picosecond width which are easy to handle and operate stably, and the use of the short pulse light source 2 enables multiphoton excitation of the sample 20 by optical pulses having a femtosecond width with a peak light intensity achieving a high fluorescent intensity. Moreover, there is used, as the short pulse light source 2, a laser diode activated through gain switch in which the repetition rate is variable, and thus a higher fluorescent intensity can be obtained by decreasing the repetition rate. Furthermore, the short pulse light source 2 and the laser scanning microscope 3 are connected via the removable single-mode optical fiber 4, which increases the degree of freedom in disposition of device and makes complicated adjustment of the free space system unnecessary, thus improving the usability.

It is noted that, in the embodiment, the negative dispersion compensation means 13 can also adjust the negative group-velocity dispersion amount so as to compensate not only the chirp amount of the incident optical pulse but also the positive group-velocity dispersion amount in a transmissive optical component such as a lens or the like disposed in the subsequent light path.

Second Embodiment

Figure 3:
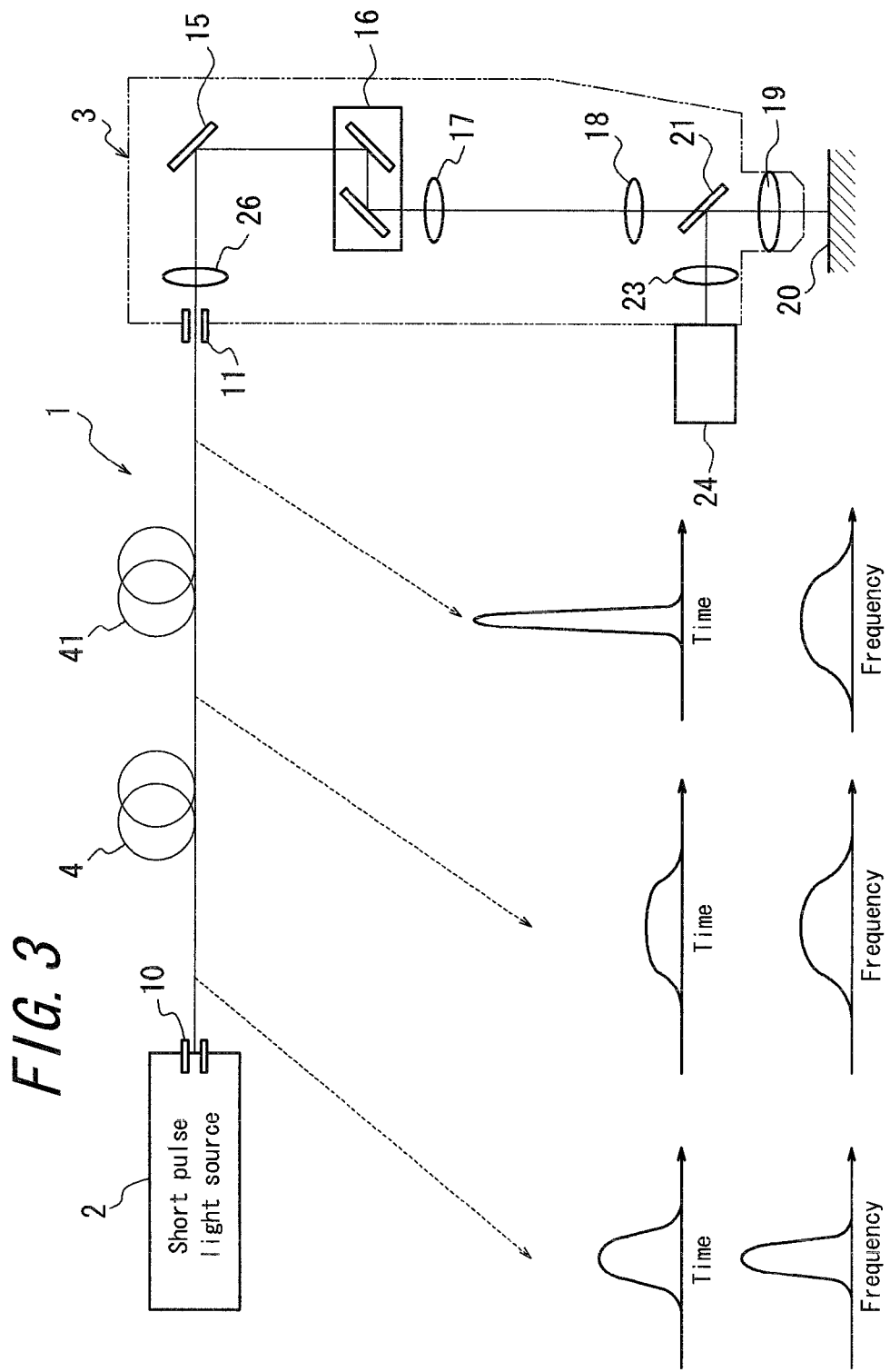
FIG. 3 is a diagram illustrating a configuration of a main part of the multiphoton-excited laser scanning fluorescence microscope system according to the second embodiment of the invention.

FIG. 3 is a diagram illustrating a configuration of a main part of the multiphoton-excited laser scanning fluorescence microscope system according to the second embodiment of the invention. With respect to the multiphoton-excited laser scanning fluorescence microscope system 1, in the configuration of the first embodiment shown in FIG. 1, instead of the negative dispersion compensation means 13, a single-mode hollow core optical fiber 41 having a hole in its cross-section is provided by connecting between the single-mode optical fiber 4 and the laser scanning microscope 3, thereby the optical pulse emitted from the single-mode optical fiber 4 passes through the single-mode hollow core optical fiber 41, the collimate lens 26 and the mirror 15 and is incident on the two-dimensional scan means 16. That is, in the embodiment, the optical pulse compression means is constituted by the single-mode optical fiber 4 and the single-mode hollow core optical fiber 41, and since other configurations and operation are the same as in the first embodiment, the components having the same function are represented with the same reference symbols, and the description thereof will be omitted.

The single-mode hollow core optical fiber 41 has a length of a few meters, for example, and has anomalous dispersion in a band with a wavelength of 980 nm. With respect to the single-mode hollow core optical fiber 41, its incidence end portion is optically and mechanically connected removably to the output end portion of the single-mode optical fiber 4 via an optical fiber connector for relay having a lens, for example, which is not shown, and its output end portion is optically and mechanically connected removably to the optical fiber connector 11 provided in the laser scanning microscope 3.

In the embodiment, the optical pulse having been incident on the single-mode optical fiber 4 is chirped (blue-shift chirped) from a long wavelength to a short wavelength by mutual interaction between SPM effects and positive GVD effects in the single-mode optical fiber 4, as described above, and then emitted. Therefore, the temporal width and the spectral width of the optical pulse emitted from the single-mode optical fiber 4 are expanded respectively as compared with those of the incident optical pulse, as schematically shown in FIG. 3, and the temporal width becomes a few picoseconds to a few tens of picoseconds, and the spectral width becomes about 5 nm to 10 nm.

The optical pulse emitted from the single-mode optical fiber 4 transmits through the single-mode hollow core optical fiber 41, thereby the blue-shift chirp is compensated by negative GVD effects in the single-mode hollow core optical fiber 41. The single-mode hollow core optical fiber 41 does not provide nonlinear optical effects such as optical Kerr effects, stimulated Raman scattering effects and the like to optical signals. Comparing optical pulses at the incidence end of the single-mode hollow core optical fiber 41 with those at the output end thereof, therefore, the optical spectral width is nearly equal, while the optical pulse width is compressed to about 300 fs and the peak light intensity of the optical pulse is increased, as schematically shown in FIG. 3.

As above, with respect to the embodiment, in the configuration of the first embodiment, the single-mode hollow core optical fiber 41 is used instead of the negative dispersion compensation means 13 so as to compress the temporal width of the optical pulse emitted from the single-mode optical fiber 4 to about 300 fs without changing the spectral width thereof, which can achieve the same effects as in the first embodiment and makes the configuration simpler as compared with the first embodiment.

Third Embodiment

Figure 4:
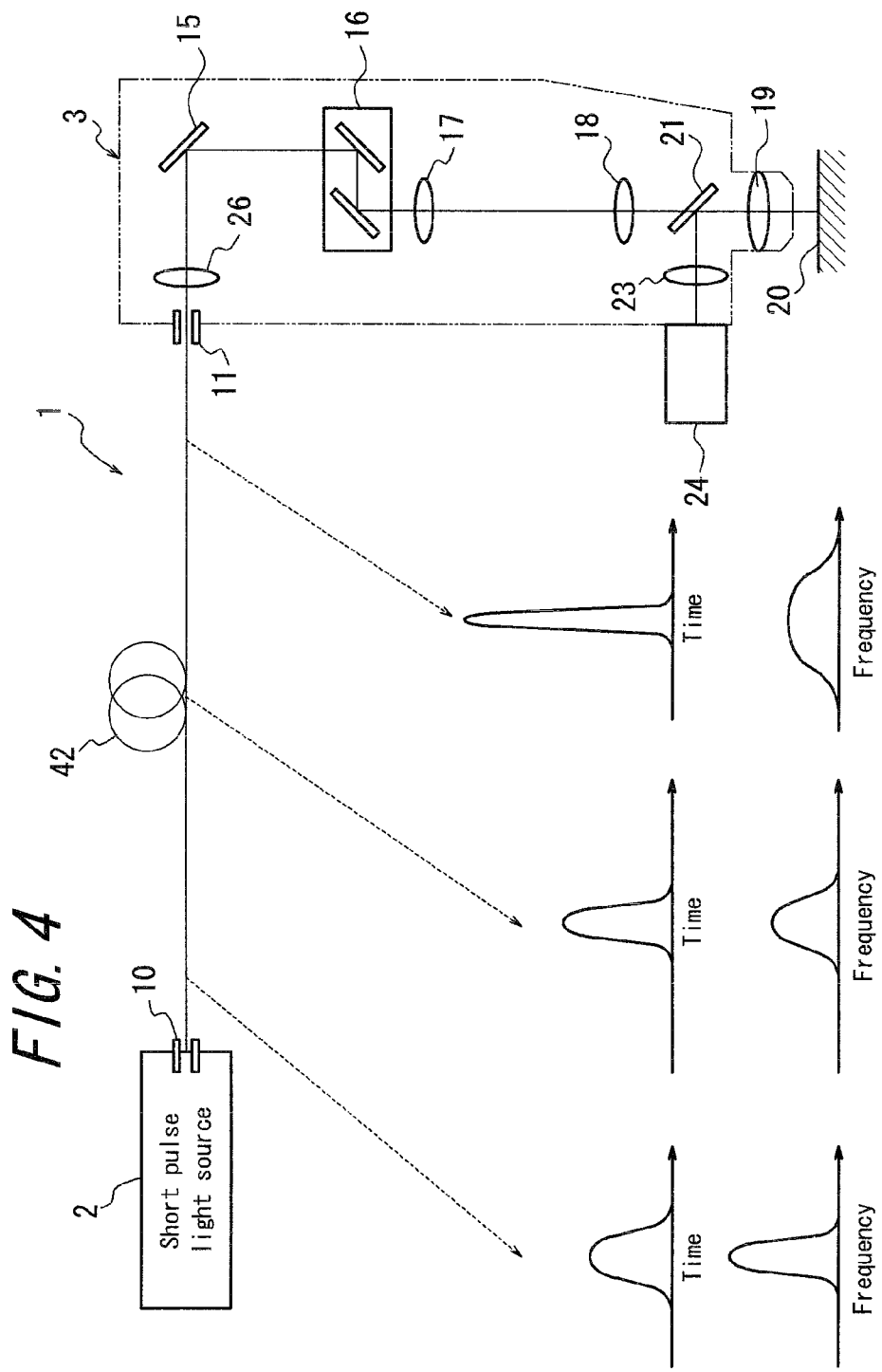
FIG. 4 is a diagram illustrating a configuration of a main part of the multiphoton-excited laser scanning fluorescence microscope system according to the third embodiment of the invention.

FIG. 4 is a diagram illustrating a configuration of a main part of the multiphoton-excited laser scanning fluorescence microscope system according to the third embodiment of the invention. With respect to the multiphoton-excited laser scanning fluorescence microscope system 1, in the configuration of the second embodiment shown in FIG. 3, the single-mode optical fiber 4 and the single-mode hollow core optical fiber 41 are replaced by a single-mode optical fiber 42 with anomalous dispersion in a wavelength band used. That is, in the embodiment, the optical pulse compression means is constituted by the single-mode optical fiber 42, and since other configurations and operation are the same as in the first embodiment, the components having the same function are represented with the same reference symbols, and the description thereof will be omitted.

As the single-mode optical fiber 42, there is used one with a length from several tens of meters to a few hundreds of meters and an anomalous dispersion value decreasing in a longitudinal direction of the fiber; one with an anomalous dispersion value at the output end being 1/10 to 1/20 of that at the incidence end, for example.

In the embodiment, the optical pulse emitted from the short pulse light source 2 passes through the single-mode optical fiber 42 with anomalous dispersion in a band with a wavelength of 980 nm. Thus, using pulse compression effects through interaction between SPM effects and negative GVD effects by the single-mode optical fiber 42, there is obtained, in the same way as in the above embodiment, the nearly TL optical pulse in which the spectral width has been expanded to about 5 nm to 10 nm and the temporal width has been compressed to about 300 fs. Such a pulse compression method is known as the adiabatic soliton compression method (see G. P. Agrawal, Nonlinear Fiber Optics, 2nd Ed., Academic Press., for example). It is noted that FIG. 4 schematically illustrates the temporal width and the spectral width of the optical pulse at the incidence end, the intermediate portion and the output end of the single-mode optical fiber 42.

As above, with respect to the embodiment, in the configuration of the second embodiment, the single-mode optical fiber 4 and the single-mode hollow core optical fiber 41 are replaced by the single-mode optical fiber 42 with anomalous dispersion in a wavelength band used so as to obtain an optical pulse having the same temporal width and spectral width and a high peak light intensity, which can achieve the same effects as in the second embodiment and makes the configuration simpler as compared with the second embodiment.

It is noted that the invention is not limited to the above embodiments, and many variations and modifications can be implemented. For example, although the short pulse light source 2 is constituted by the gain switched laser diode 6, it can be constituted using various kinds of solid-state laser (titanium-sapphire laser or the like, for example), fiber laser or the like capable of generating optical pulses with a width of picoseconds or femtoseconds.

Figure 5:
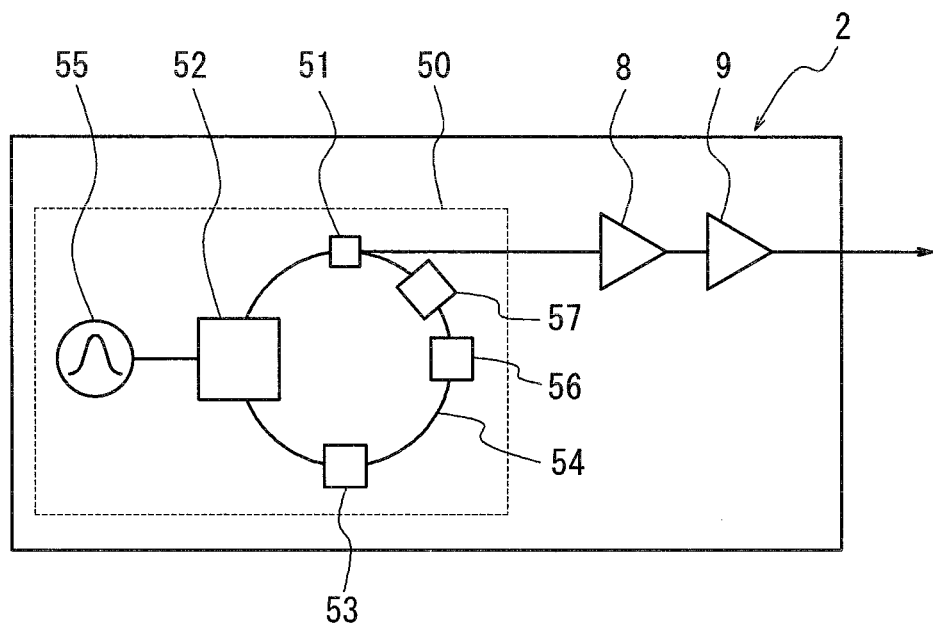
FIG. 5 is a schematic configuration diagram illustrating another example of the short pulse light source which can be used in the first to third embodiments.
Figure 6:
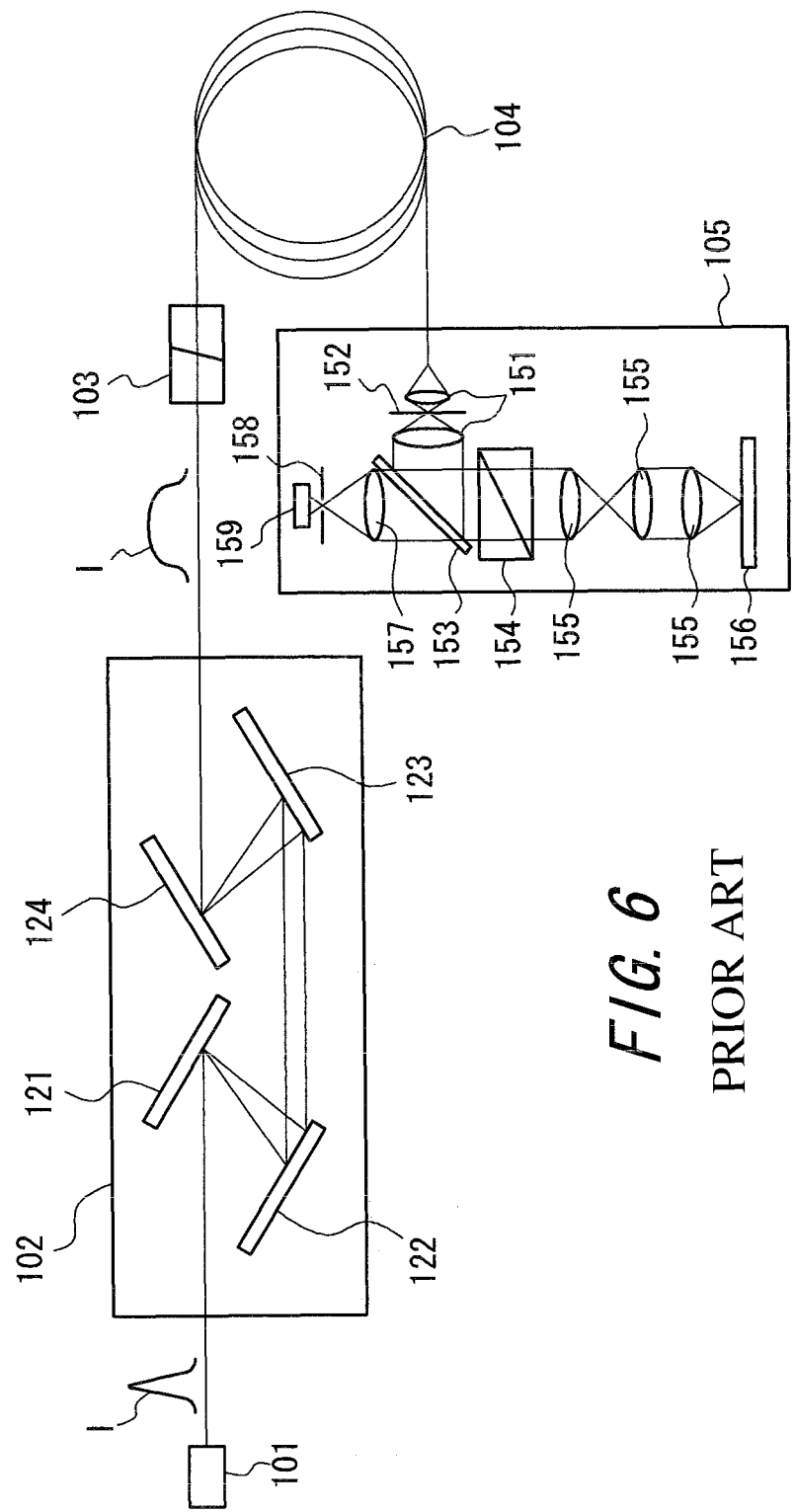
FIG. 6 is a diagram illustrating a configuration of a conventional multiphoton-excited microscope system.

FIG. 5 is a schematic configuration diagram of the short pulse light source 2 using an active-mode locked fiber-ring laser. The short pulse light source 2 has an active-mode locked fiber-ring laser 50, the fiber amplifiers 8, 9 and the optical fiber connector 10 shown in FIG. 2. The active-mode locked fiber-ring laser 50 has a demultiplexing coupler 51, a gain unit 52, a band-pass filter 53, an isolator 56 and a dispersion compensation means 57, and a single-mode optical fiber 54 connects these optical components in a ring shape. Furthermore, the active-mode locked fiber-ring laser 50 has a signal generator 55 connected to the gain unit 52.

The gain unit 52 comprises a gain medium constituted by a rare-earth-doped fiber and an intensity modulator constituted by an LN (LiNbO3) modulator. Here, the rare-earth-doped fiber is a Yb-doped single-mode optical fiber. A WDM (wavelength division multiplex) coupler which is not shown is connected to the rare-earth-doped fiber, and a laser diode as a light source for excitation which is not shown is optically connected to the multiplex side of the WDM coupler. Here, the laser diode is one continuously oscillating light having a wavelength of 915 nm, and light from the laser diode is absorbed by the Yb-doped fiber through the WDM coupler to generate a gain for a band of 980 nm.

The demultiplexing coupler 51 demultiplexes incident light at a designed ratio, and the demultiplexing ratio to a single-mode optical fiber 54 corresponds to the reflectance and the demultiplexing ratio to the fiber amplifier 8 corresponds to the transmittance.

The dispersion compensation means 57 has a negative dispersion amount to cancel positive dispersion of the single-mode optical fiber 54 and the gain medium in the gain unit 52, thereby the whole of the ring portion of the active-mode locked fiber-ring laser 50 is rendered to be in a zero dispersion state so that the circulating velocity is not varied depending on a wavelength.

The isolator 56 makes light transmit in an only one direction. In the embodiment, light in a clockwise direction in FIG. 5, that is, light from the dispersion compensation means 57 is transmitted only to a direction of the band-pass filter 53, and light in the opposite direction is not allowed to pass through.

The band-pass filter 53 exerts transmissive properties for specific wavelength bands, which causes spontaneous emission light having a wide range of wavelength band to cut therethrough and inhibits lasing due to light having the different wavelength.

The signal generator 55 is connected to the intensity modulator of the gain unit 52 to modulate temporal transmissive properties of the gain unit 52.

In the above configuration, spontaneous emission light emitted from the gain unit 52 transmits, via the single-mode optical fiber 54, through the demultiplexing coupler 51, the dispersion compensation means 57, the isolator 56 and the band-pass filter 53 in this order, reaching the Yb-doped fiber of the gain unit 52 again to be amplified. The spontaneous emission light is lased when a gain of the gain unit 52 exceeds the total of transmittance of the demultiplexing coupler 51 and other losses and the light has been amplified through repetitive transmission process on the ring-shaped path, and the laser light is emitted from the demultiplexing coupler 51 to the fiber amplifier 8.

Here, the signal generation frequency of the signal generator 55 connected to an intensity modulator which is not shown is set so that the temporal width and the timing of gain generation by the gain unit 52 correspond with the time interval where spontaneous emission light travels around on the ring-shaped path connected via the single-mode optical fiber 54 at the time of gain generation and reaches the gain unit 52 again, which enables the mode-locked state. In this case, laser light emitted from the demultiplexing coupler 51 to the fiber amplifier 8 is pulse light having the same repetition rate as the signal generation frequency of the signal generator 55.

Furthermore, the optical pulse of laser light oscillated from the active-mode locked fiber-ring laser 50 can be a short pulse light having a temporal width of a few picoseconds by traveling around on the above ring-shaped path repeatedly. With respect to the mode-locked state, moreover, a fundamental state thereof is defined by a case in which one optical pulse is existent in a ring-shaped path connected via the single-mode optical fiber 54, while two or more optical pulses can be existent. This is enabled by setting a frequency of the signal generator 55 to an integral multiple of that at the fundamental state. Thus, the repetition rate of the optical pulse can be adjusted to an integral multiple of the frequency of the optical pulse at the fundamental state.

As above, short pulse light emitted from the active-mode locked fiber-ring laser 50 is amplified by two fiber amplifiers 8, 9 to have an average light intensity (average output) of several tens of mW to a few W and output from the short pulse light source 2.

According to the short pulse light source 2 having the configuration shown in FIG. 5, it becomes possible to instantaneously control the repetition rate of the optical pulse emitted from the short pulse optical pulse 2 easily and stably only by changing the time interval in repetition for modulated electrical signals applied to the intensity modulator of the active-mode locked fiber-ring laser 50. It is noted that, in FIG. 5, the gain unit 52 is constituted not only by a combination of a rare-earth-doped fiber as a gain medium and an intensity modulator but also by using a gain medium and a semiconductor optical amplifier serving also as a modulation means, for example.

Furthermore, the multiphoton-excited measuring device of the invention can be applied not only to a multiphoton-excited laser scanning fluorescence microscope system measuring living cells described in the above embodiment but also effectively to a microscope system for avoiding heat damages to a sample due to optical pulse irradiation therefor particularly when a deep portion or a strong scatterer is observed. In addition, the multiphoton-excited measuring device of the invention can be applied to a measuring device measuring other samples such as semiconductor materials or the like through multiphoton excitation (nonlinear excitation).

The invention claimed is:

1. A multiphoton-excited measuring device measuring a biological sample with the use of a multiphoton absorption phenomenon by optical pulses having high intensity, comprising
    a short pulse light source emitting optical pulses, a repetition rate of which is variable;
    an irradiation optical system irradiating a sample with optical pulses emitted from the short pulse light source;
    a detector detecting signal light generated, in association with multiphoton excitation, from the sample by the irradiation with optical pulses; and
    an optical pulse compression unit being disposed between the short pulse light source and the irradiation optical system and including an optical fiber solely constituted by a single-mode optical fiber transmitting optical pulses emitted from the short pulse light source with anomalous dispersion in a wavelength to compress a pulse width, with the use of nonlinear effects causing intensity-dependent spectral variation of the optical fiber, so that a pulse width of optical pulses with which the sample is to be irradiated is shortened to equal to or narrower than that of optical pulses emitted from the short pulse light source and so that a spectral width of optical pulses with which the sample is to be irradiated is broader than that of optical pulses emitted from the short pulse light source.

2. A multiphoton-excited measuring device according to claim 1,
    wherein the optical fiber included in the optical pulse compression unit expands a spectral width and provides positive group-velocity dispersion for optical pulses emitted from the short pulse light source; and
    the optical pulse compression unit comprises a negative dispersion compensation unit providing negative group-velocity dispersion for optical pulses having transmitted through the single-mode optical fiber.

3. A multiphoton-excited measuring device according to claim 2, wherein the negative dispersion compensation unit comprises any one of a pair of diffraction gratings, a pair of prisms or a pair of grisms.

4. A multiphoton-excited measuring device according to claim 1,
    wherein the optical fiber included in the optical pulse compression unit is constituted by a single-mode optical fiber expanding a spectral width and providing positive group-velocity dispersion for optical pulses emitted from the short pulse light source; and
    the optical pulse compression unit comprises a single-mode hollow core optical fiber with a hole in a cross-section thereof providing negative group-velocity dispersion for optical pulses having transmitted through the single-mode optical fiber.

5. A multiphoton-excited measuring device according to claim 1, wherein the optical fiber included in the optical pulse compression unit is constituted by a single-mode optical fiber expanding a spectral width and providing negative group-velocity dispersion for optical pulses emitted from the short pulse light source.

6. A multiphoton-excited measuring device according to claim 1, wherein a pulse width of optical pulses emitted from the short pulse light source is of picosecond and a pulse width of optical pulses with which the sample is irradiated is of femtosecond.

7. A multiphoton-excited measuring device according to claim 1, wherein the short pulse light source comprises a gain switched laser diode.

8. A multiphoton-excited measuring device according to claim 1, wherein the short pulse light source comprises an active-mode locked fiber-ring laser.

9. A multiphoton-excited measuring device according to claim 1, wherein the optical pulse compression unit is removable.

10. A multiphoton-excited measuring device according to claim 1, wherein the multiphoton-excited measuring device is a multiphoton-excited fluorescence microscope system detecting, by the detector, fluorescence generated from the sample in association with multiphoton excitation.

* * * * *